United States Patent [19]

McCaully et al.

[11] Patent Number: 4,506,077

[45] Date of Patent: Mar. 19, 1985

[54] TIN COMPLEXES OF INDOLINE-2-CARBOXYLIC ACIDS AND ESTERS PREPARED FROM O-NITROPHENYLPYRUVIC ACIDS AND ESTERS

[75] Inventors: Ronald J. McCaully, Malvern; Dong H. Kim, Wayne, both of Pa.

[73] Assignee: American Home Products Corporation, New York, N.Y.

[21] Appl. No.: 463,428

[22] Filed: Feb. 3, 1983

[51] Int. Cl.³ .......................................... C07D 209/18
[52] U.S. Cl. ................................... 548/402; 548/508
[58] Field of Search ............................... 548/402, 508

[56] References Cited

PUBLICATIONS

W. J. Houlihan, ed., *Indoles, Part One*, pp. 396–399 (Wiley Interscience, New York, 1972).
Nolande, et al., "Ethyl Indole-2-Carboxylate", *Organic Synthesis*, vol. 43, pp. 40–45 (J. Wiley & Sons, New York, 1963).
Robinson, B., "The Reduction of Indoles and Related Compounds", Chem. Reviews, 69, 785, 785–7 (1969).
Elderfield, R. C., ed., *Heterocyclic Compounds*, vol. 3, pp. 18–22 and 46–51 (John Wiley & Sons, Inc., New York, 1952).
Corey et al., "Studies in Asymmetric Synthesis of α-amino Acids", J. Am. Chem. Soc., 92, 2476, 2480 (1970).
Hudson et al., "The Synthesis and Chemistry of DL-indoline-2-carboxylic Acid", Aust. J. Chem., 20, 1935–1941 (1967).

*Primary Examiner*—Glennon H. Hollrah
*Assistant Examiner*—D. B. Springer
*Attorney, Agent, or Firm*—Arthur G. Seifert

[57] ABSTRACT

Disclosed herein is a process for obtaining indoline-2-carboxylic acid ester tin complexes directly from o-nitropyruvic acids using metallic tin and dry hydrogen chloride gas in a lower alkanol solvent, at atmospheric pressures.

4 Claims, No Drawings

TIN COMPLEXES OF INDOLINE-2-CARBOXYLIC ACIDS AND ESTERS PREPARED FROM O-NITROPHENYLPYRUVIC ACIDS AND ESTERS

Indoline-2-carboxylic acids are used as the starting material in the preparation of N-(3-mercapto-2-alkyl-1-oxopropyl)-2,3-dihydro-1H-indole-2-carboxylic acids which exhibit pharmacological properties as angiotensin converting enzyme (ACE) inhibitors and as antihypertensive agents, as shown in U.S. Pat. No. 4,303,583.

In the past, indoline-2-carboxylic acid ethyl ester has been obtained by reduction of the corresponding indole-2-carboxylic acid ethyl ester. One such reduction, described by Corey et al., Journal of the American Chemical Society, 92, 2476–2488, at 2480 (1970), uses metallic tin and dry hydrogen chloride gas in ethanol in a high pressure sealed bomb. In this reduction, the indoline-2-carboxylic acid ethyl ester is obtained first as a tin complex which is isolated and treated with anhydrous ammonia to obtain the desired indoline-2-carboxylic acid ethyl ester. The ester is then hydrolyzed by conventional methods to obtain the free acid.

One means of preparing the indole-2-carboxylic acid ethyl ester to be used in the Corey et al. reduction process is via the Reissert indole synthesis, in which o-nitrophenylpyruvic acid or its ethyl ester is reductively cyclized with ferrous sulfate and ammonia. The Reissert indole synthesis is described in W. J. Houlihan, ed., *Indoles, Part One*, pp. 396–399 (Wiley Interscience, New York, 1972).

Thus, at present, a two-step process is required to obtain the intermediate indoline-2-carboxylic acid ester tin complex when o-nitrophenylpyruvic acid (or ester) is used as the starting material, as shown in route 1, reactions 1a and 1b of Chart I below.

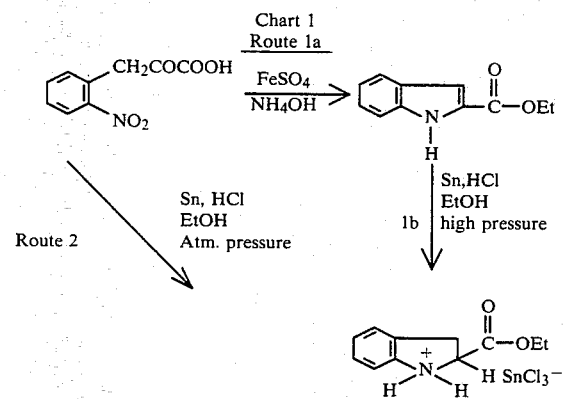

As seen from route 2, above, Applicants' process requires only one step to obtain the indoline-2-carboxylic acid ethyl ester tin complex from the o-nitrophenylpyruvic acid starting material. Moreover, Applicants' one step, although utilizing metallic tin and hydrogen chloride gas as in the step 1b indole-2-carboxylic acid ester reduction, does not require a high pressure, sealed bomb reaction vessel.

Unexpectedly, Applicants have discovered that the reductive cyclization of o-nitrophenylpyruvic acid can be carried out using metallic tin and dry hydrogen chloride gas at atmospheric pressures to yield directly the desired indoline-2-carboxylic acid ester tin complex. Additionally, Applicants have discovered that the amount of hydrogen chloride gas can be greatly reduced from that used in the indole-2-carboxylic acid ethyl ester reduction of Corey et al.—even though Applicants' process is carried out at atmospheric pressures and is a double reduction. Although the Corey et al. reduction begins with the ethyl ester of indole-2-carboxylic acid, Applicants were not successful in obtaining the indoline-2-carboxylic acid ethyl ester tin complex when they started with the ethyl ester of o-nitropyruvic acid.

DETAILED DESCRIPTION OF THE INVENTION

The invention for which patent protection is sought is a process for preparing a tin complex of an indoline-2-carboxylic acid ester of the formula:

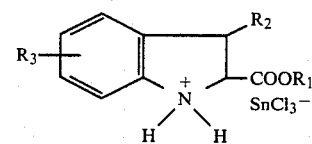

wherein:
  $R_1$ is a lower alkyl group;
  $R_2$ is hydrogen or a lower alkyl group; and
  $R_3$ is hydrogen, a lower alkyl group, a lower alkoxy group, or a halogen;

which process comprises contacting an o-nitrophenylpyruvic acid of the formula:

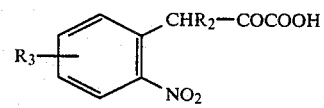

wherein $R_2$ and $R_3$ are as defined above, with metallic tin and dry hydrogen chloride gas in a lower alkanol of the formula $R_1OH$, wherein $R_1$ is as defined above, at atmospheric pressures. The tin complex is isolated and may then be converted to the free indoline-2-carboxylic acid ester by conventional means, for example, by dissolution in absolute ethanol and treatment with anhydrous ammonia until the pH of the solution reaches 8 (Corey et al., J. Am. Chem. Soc., 92, 2476, 2480 (1970)). Preferred processes are those wherein $R_2$ or $R_3$ are hydrogen. Further preferred processes are those wherein $R_1$ is methyl or ethyl with ethyl being most preferred.

The tin metal used in this process is used at a ratio of about 4 moles of tin per mole of α-nitrophenylpyruvic acid (or ester) starting material. The ratio of HCl (gas)+$R_1OH/R_1OH$ (i.e. final volume of solvent plus dissolved gas to initial volume of solvent) is in the range of 1.35–1.65. The preferred range for this ratio is 1.35–1.45. (This compares with a ratio of 1.94 used by Corey et al., supra).

Particularly, during the dissolution of the dry hydrogen chloride gas in the absolute alcohol, the temperature of the reaction vessel is kept low with cooling in a dry ice-acetone bath (about −60° to −70° C.). When the starting tin metal and starting o-nitropyruvic acid are added and then allowed to react initially (up to 6 hours), the reaction mixture temperature is maintained in the −40° to −70° range, depending upon the progress of the reaction. Thereafter, the reaction mixture temperature is allowed to rise to room temperature until the reaction is deemed completed.

The process and mode of carrying out the invention are further illustrated by the following example.

EXAMPLE 1

Preparation of 2,3-Dihydro-1H-Indole-2-Carboxylic Acid Ethyl Ester Tin Chloride Hydrochloride Complex From o-Nitrophenylpyruvic Acid A 5-liter flask equipped with an overhead stirrer, a low temperature thermometer, a nitrogen inlet, a gas inlet bubbler tube, and a Raschig ring gas scrubber was chilled in a dry ice-acetone bath to $-60°$ C. and charged with 1500 ml. of absolute ethanol. Gaseous hydrogen chloride was added to the ethanol until the volume increased to 2150 ml. The volume increase corresponds approximately to 1.2 kg. of hydrogen chloride. To the chilled mixture was added 104.6 g. (0.50 mole) of o-nitrophenylpyruvic acid and 250 g. (2.10 mole) of tin metal (30 mesh). The mixture was stirred at $-40°$ C. for several hours and allowed to warm to room temperature overnight to afford a clear orange-amber solution. The volume of the solution was concentrated to 800 ml., and concentrate was allowed to stand for 16 hours at 5° C. The crystalline solid that separated was filtered and dried at 60° C. over phosphorous pentoxide in vacuo to afford 119 g. (57%) of the above titled product, m.p. 114°–116° C. Recrystallization from ethyl acetate elevates the melting point of the complex to 117°–119° C.

What is claimed is:

1. A process for the preparation of indoline-2-carboxylic acid ester tin complex of the formula:

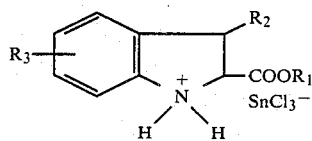

wherein
 $R^1$ is a lower alkyl group;
 $R^2$ is hydrogen or a lower alkyl group; and
 $R^3$ is hydrogen, a lower alkyl group, a lower alkoxy group, or a halogen, which comprises contacting an o-nitrophenylpyruvic acid or ester of the formula:

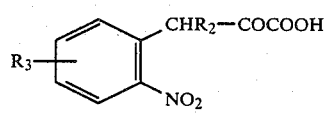

wherein $R_2$ and $R_3$ are as defined above, with metallic tin and dry hydrogen chloride in a lower alkanol of the formula $R_1OH$, wherein $R_1$ is as defined above, at atmospheric pressures.

2. A process according to claim 1 wherein $R_2$ is hydrogen.

3. A process according to claim 1 wherein $R_1$ is ethyl.

4. A process according to claim 1 wherein $R_2$ and $R_3$ are hydrogen and $R_1$ is methyl or ethyl.

* * * * *